United States Patent
Zhu et al.

(10) Patent No.: US 8,227,750 B1
(45) Date of Patent: Jul. 24, 2012

(54) METHOD AND APPARATUS FOR NANO-CAPILLARY/MICRO ELECTROSPRAY FOR USE IN LIQUID CHROMATOGRAPHY-MASS SPECTROMETRY

(75) Inventors: Yixin Zhu, Auburn, CA (US); Kerry D. Nugent, Penn Valley, CA (US)

(73) Assignee: Bruker-Michrom, Inc., Auburn, CA (US)

(*) Notice: Subject to any disclaimer, the term of this patent is extended or adjusted under 35 U.S.C. 154(b) by 337 days.

(21) Appl. No.: 12/387,094

(22) Filed: Apr. 27, 2009

Related U.S. Application Data

(60) Provisional application No. 61/125,802, filed on Apr. 28, 2008.

(51) Int. Cl.
*B01D 59/44* (2006.01)
*H01J 49/00* (2006.01)

(52) U.S. Cl. ........ 250/288; 250/281; 250/282; 250/283; 250/287; 250/289; 250/290; 250/291; 250/292

(58) Field of Classification Search .......... 250/281–283, 250/287–292
See application file for complete search history.

(56) References Cited

U.S. PATENT DOCUMENTS

| | | | |
|---|---|---|---|
| 4,861,988 A | 8/1989 | Henion | |
| 5,130,538 A | 7/1992 | Fenn | |
| 5,412,208 A | 5/1995 | Covey | |
| 5,432,343 A | 7/1995 | Gulcicek | |
| 5,504,329 A | 4/1996 | Mann | |
| 5,788,166 A | 8/1998 | Valaskovic | |
| 6,068,749 A | 5/2000 | Karger | |
| 6,140,640 A * | 10/2000 | Wittmer et al. | 250/288 |
| 6,177,669 B1 * | 1/2001 | Wells et al. | 250/288 |
| 6,297,499 B1 | 10/2001 | Fenn | |
| 6,753,521 B1 | 6/2004 | Park | |
| 6,992,299 B2 | 1/2006 | Lee | |
| 2006/0054806 A1 * | 3/2006 | Yamada et al. | 250/288 |

* cited by examiner

*Primary Examiner* — Jack Berman
*Assistant Examiner* — Meenakshi Sahu
(74) *Attorney, Agent, or Firm* — Heisler & Associates

(57) ABSTRACT

An ion injection spray apparatus and method are provided for coupling a liquid chromatograph or other liquid flow device to a mass spectrometer. The ion injection spray assembly is composed in part of a chamber for voltage and gas input, a metal union for a liquid voltage junction, a gas distribution assembly, a vacuum seal and an ion spray needle. The position of the ion spray needle within this assembly is directly coupled to the outlet of the upstream liquid flow device through the metal union. The vacuum of the mass spectrometer pulls gas at atmospheric pressure though the gas distribution assembly to focus the sample liquid at the spray needle outlet and create a centrifugal gas funnel which helps to desolvate the sample ions and sweep them into the mass spectrometer over a wide range of flow rates.

30 Claims, 3 Drawing Sheets

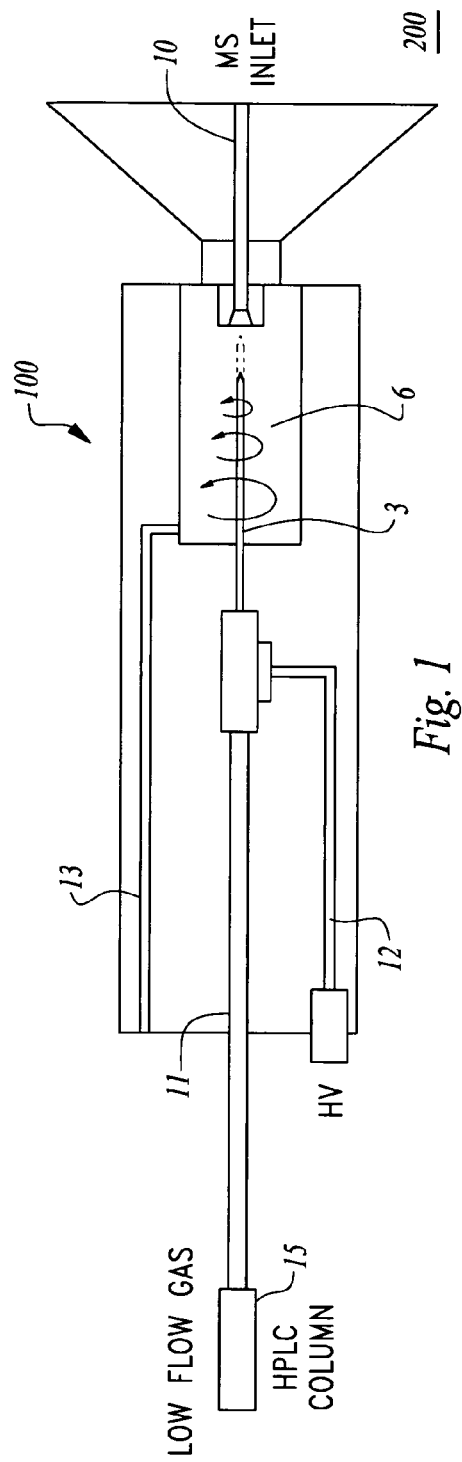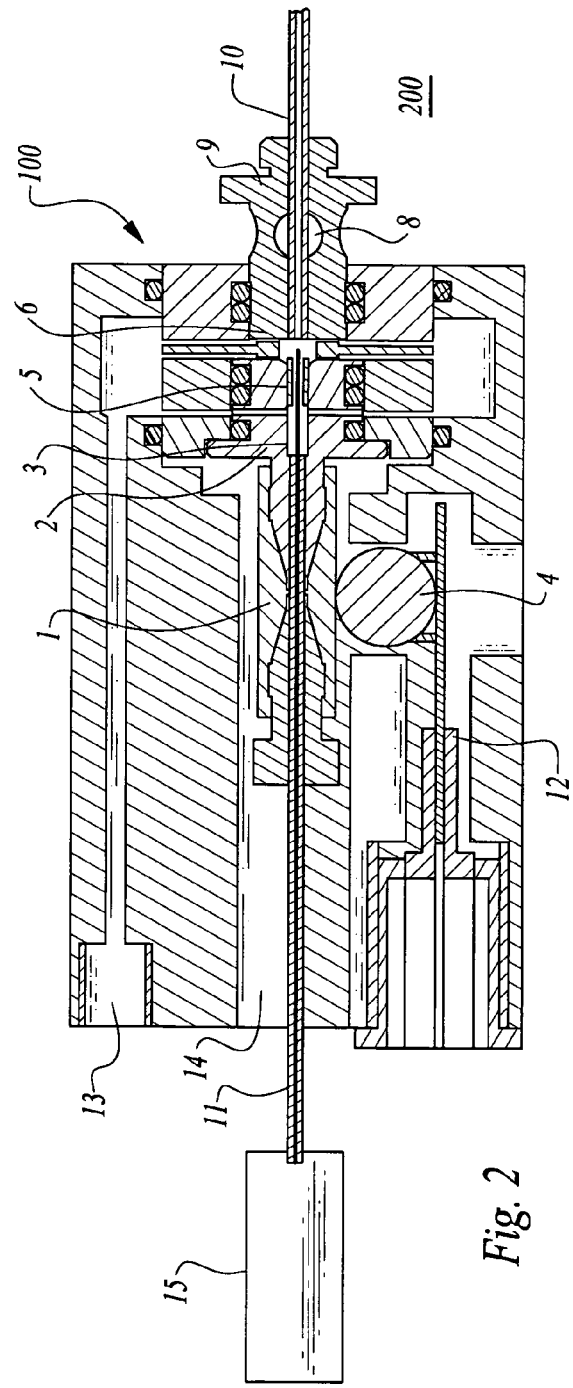

METHOD AND APPARATUS FOR NANO-CAPILLARY/MICRO ELECTROSPRAY FOR USE IN LIQUID CHROMATOGRAPHY-MASS SPECTROMETRY

CROSS-REFERENCE TO RELATED APPLICATIONS

This application claims benefit under Title 35, United States Code §119(e) of U.S. Provisional Application No. 61/125,802 filed on Apr. 28, 2008.

FIELD OF THE INVENTION

The present invention relates generally to liquid chromatography (LC) and mass spectrometry (MS) systems and the analysis of chemical samples, and more particularly to ion injection spray devices for use in LC/MS. More particularly, this invention relates to ionization of a sample from an LC device that uses centrifugal gas flow to keep the ionized sample concentrated along a flow path before entering the MS device.

BACKGROUND OF THE INVENTION

The present invention relates to electrospray ionization (ESI) devices or other ion injection spray devices for use in LC/MS. LC/MS is an important tool in the analysis of many chemical compounds including biomolecules which are important to human health and longevity. Specifically, LC/MS can be used to isolate, identify, characterize and quantify a wide range of sample molecules. The analysis of samples by LC/MS consists of four main steps; 1) LC separation of the different molecules in a sample, 2) formation and desolvation of sample molecule ions, 3) mass analysis to separate the ions from one another according to their mass to charge ratios, and 4) detection of the ions. A variety of means exist in the field of LC/MS to perform each of these functions. The particular combination of means used in a given LC/MS system determines the characteristics of that specific system.

To mass analyze ions, for example, one might use an ion trap analyzer, where ions are trapped by a radio frequency (RF) quadrupole field and mass selective ejected by scanning RF amplitude and/or dc voltage. Other mass analyzers include the quadrupole (Q), the ion cyclotron resonance (ICR), the sector (using a magnetic or electrostatic field or both), and the time of flight (TOF) analyzers.

Before mass analysis can begin, however, gas phase ions must be formed from the sample molecules. If the sample molecules are sufficiently volatile, ions may be formed by electron impact (EI) or chemical ionization (CI). For solid samples, ions can be formed by desorption/ionization of the sample molecules by bombardment with high energy particles. For liquid phase sample molecules, atmospheric pressure ionization (API) is currently the technique of choice. One of the more widely used API methods, known as electrospray ionization (ESI), was first suggested by Dole et al. (M. Dole, L. L. Mack, R. L. Hines, R. C. Mobley, L. D. Ferguson, M. B. Alice, J. Chem. Phys. 49, 2240, 1968). In ESI, analytes in solution and sprayed from a needle and the spray is induced by the application of a potential difference between the spray tip (where the liquid emerges) and a counter electrode. By subjecting the emerging liquid to a strong electric field, it becomes charged, and as a result, it "breaks up" into smaller particles if the charge imposed on the liquid's surface is strong enough to overcome the surface tension of the liquid (i.e., as the particles attempt to disperse the charge and return to a lower energy state). This results in the formation of fine, charged droplets of solution containing the analyte molecules. These droplets further evaporate leaving behind gas phase analyte ions.

Electrospray mass spectrometry (ESI-MS) was introduced by Yamashita and Fenn (M. Yamashita and M. B. Fenn, J. Phys. Chem. 88, 4671, 1984). To establish this combination of ESI and MS, ions had to be formed at atmospheric pressure, and then introduced into the vacuum system of a mass analyzer via a differentially pumped interface. The combination of ESI and MS afforded scientists the opportunity to mass analyze a wide range of samples, and ESI-MS is now widely used in the analysis of biomolecules and other complex organic molecules.

Over the past two decades, a number of means and methods of electrospray useful to LC/MS have been developed. For higher LC flow rates (i.e. 50-5000 ul/min), pneumatic assisted electrospray has become the technique of choice (A. P. Bruins, T. R. Covey, and J. D. Henion, Anal. Chem., 59, 2642, 1987, and Henion et al, U.S. Pat. No. 4,861,988). This technique uses a gas flowing past the ESI spray tip to assist in the formation and desolvation of charged droplets. Although the gas assists in the formation of the spray and makes the operation of the electrospray ionization (ESI) easier and more robust, the excess gas dilutes the sample ions, resulting in lower ion transfer efficiency and a loss of sensitivity.

For lower flow LC/MS (10-1000 nl/min), nanospray ionization (NSI) has become the technique of choice (M. S. Wilm and M. Mann, Int. J. Mass Spectrom. Ion Processes, 136-167, 1994; and M. Mann and M. S. Wilm, U.S. Pat. No. 5,504,329). U.S. Pat. No. 5,504,329 is incorporated herein by reference in its entirety, with various details of NSI being utilized with the apparatus and method of this invention. NSI utilizes very low liquid flows and a very narrow spray tip outlet placed very close to the MS inlet, which results in the formation of very small spray droplets which can be desolvated without gas assistance. Although the ion signal provided by NSI in conjunction with MS is essentially the same as with conventional ESI, MS is a concentration sensitive detection technique which makes NSI the best technique for high sensitivity applications. Since no gas is used in NSI, high ion transfer efficiency can be achieved, but at a cost of ease of use and robustness relative to pneumatic assisted electrospray.

When using NSI-MS, the liquid flow rate, solvent composition, spray tip voltage, spray tip design, spray tip integrity and the position of the spray tip outlet relative to the MS inlet are all critical for good spray stability which results in proper ionization, desolvation and ion transfer efficiency. NSI spray tips are generally made by pulling and cutting fused silica tubing to make the very small ID/OD tips required for stable spray at nanoliter per minute flow rates, but these tips are difficult to reproduce, fragile to handle and easy to clog. Because of these limitations, NSI can be difficult to set up and maintain, making it poorly suited for analyses requiring robust operation.

Since NSI is generally limited to flow rates below 1 μl/min, samples must be separated using nanoLC which has its own share of problems and limitations. NanoLC requires specialized instrumentation and careful attention to details to insure optimal performance. NanoLC columns (<150 um ID) have limited sample capacity, require specialized sample injection protocols to load large sample volumes and lack the robustness of larger LC columns. Finally, the low flow rates used in nanoLC/NSI-MS typically result in longer sample analysis time, making this technique poorly suited to high throughput applications like biomarker validation and pharmaceutical development.

Several attempts have been made to develop commercially viable microspray ionization (MSI) sources in an effort to overcome the limitations imposed by NSI, but these MSI sources have not been very well accepted. Although these MSI sources, which are basically miniaturized versions of pneumatic assisted ESI, do offer increased stability and work at higher LC flow rates versus NSI, the added gas flow still results in a lower ion transfer efficiency and a unacceptable loss in sensitivity for most researchers.

The applicants have recognized the need for a LC/MS electrospray apparatus and method that can overcome the limitations imposed by ESI, MSI and NSI, without compromising the ion transfer efficiency critical to high sensitivity applications. This apparatus and method provide simple, robust operation over a wide dynamic flow range and maintain high ion transfer efficiency independent of the LC flow rate. This apparatus and method can be be simple to set up and use ("Plug and Play"), operate continually with minimal maintenance and provide both high sensitivity and high throughput operation, especially at flows from 0.1-100 ul/min.

SUMMARY OF THE INVENTION

To achieve the foregoing objectives of the present invention, an ion injection spray device and method for introducing sample ions into a mass spectrometer is presented. The assignee of this invention, Michrom BioResources, Inc. of Auburn, Calif., refers to its brand of this ion injection spray device by the trademark CAPTIVES PRAY. It is an object of the invention to provide a simply constructed, easy to operate and highly efficient mass spectrometer sample introduction apparatus for a wide range of liquid sample flow rates. An apparatus according to the present invention comprises a spray needle with an inlet opening for acceptance of a liquid flow, such as from the output of an LC device and an outlet tip for spray of said liquid into the MS. The spray needle preferably terminates in an ion injection spray device (akin to an electrospray needle) for the creation of charged particles of the liquid flow for introduction into the MS. Upon exiting the outlet tip of the spray needle, the charged particles of the liquid flow are introduced to the MS inlet. The ions are drawn by an electric field from the spray tip and are focused by gas pulled in by the vacuum of the mass spectrometer.

According to the invention, liquid from a liquid chromatograph (LC) or other liquid flow device flows through a column into a metal union. The device comprises a spray needle preferably of circular cross-section, encircled by a non-conductive outer tube also preferably of circular cross-section.

Unlike NSI technology, the present invention allows the practitioner to easily attach the spray assembly to the MS. There is no need for microscopes, cameras or X,Y,Z positioning adjustment. Rather the spray assembly is simply attached to the MS inlet with a vacuum seal and is ready to perform its function within the MS. The present invention reduces set-up time and increases the speed in which mass spectrometry can be carried out versus NSI-MS. The present invention provides stable spray and uniform performance across a wide dynamic flow rate range (0.1-100+ ul/min).

Coaxial gas flow is preferably introduced around the spray needle through an annular space between the spray needle and outer tube at high velocity, typically generated by the vacuum inlet of the MS. A second gas flow is preferably introduced at the spray needle outlet to focus the spray inward and a third gas flow is introduced in a centrifugal fashion to provide funnel-shaped swirling gas flow to help desolvate and focus the ions into the MS. The device of the present invention is preferably sealed by at least one O-ring to generate vacuum assisted gas flow and prevent loss of sample ions into the atmosphere. Unlike previous electrospray technology where the spray and drying gases are open to the atmosphere, the present invention uses the vacuum from MS to guide the flow of ions and gases in the sealed spray chamber into the MS and prevent loss of sample ions to the atmosphere.

The metal (or other electrically conductive material) union is either connected to high voltage with the MS inlet at ground or the union is at ground and the MS inlet is connected to high voltage, and the voltage differential is generally between 500 and 5000 volts. Typically the position of the outlet tip of the spray needle is fixed at 1-5 mm from the MS inlet capillary or orifice. The combination of the electric field and the gas flows serve to nebulize the liquid stream as it exits the spray needle. The apparatus and method described by this invention and shown in the figures that follow has been tested and found to meet all of the performance criteria outlined above.

OBJECTS OF THE INVENTION

Accordingly, a primary object of the present invention is to provide an ion injection spray device which can effectively convert samples such as those discharged from a liquid chromatograph (LC) into ions before passage into a mass spectrometer (MS).

Another object of the present invention is to provide a method for ionizing a sample between an upstream source, such as a LC and a mass analyzer, such as a MS.

Another object of the present invention is to provide a sample evaluation system which includes a LC, an ion injection spray device and a MS which reliably pass samples from the LC to the MS.

Another object of the present invention is to provide an ion injection spray device which is easy to align with an inlet to a MS or other subatmospheric pressure mass analyzer.

Another object of the present invention is to provide an ion injection spray device which utilizes centrifugal flow of a gas adjacent an outlet of a spray needle to assist in keeping ions to be mass analyzed along a central axis flow path.

Another object of the present invention is to provide an ion injection spray device which has a wide dynamic flow range, such as for between 0.1 and 100 or more microliters per minute.

Other further objects of the present invention will become apparent from a careful reading of the included drawing figures, the claims and detailed description of the invention.

BRIEF DESCRIPTION OF THE DRAWINGS

A further understanding of the present invention can be obtained by reference to a preferred embodiment set forth in the illustrations of the accompanying drawings. Although the illustrated embodiment is merely exemplary of systems for carrying out the present invention, both the organization and method of operation of the invention, in general, together with further objectives and advantages thereof, may be more easily understood by reference to the drawings and the following description. The drawings are not intended to limit the scope of this invention, which is set forth with particularity in the claims as appended or as subsequently amended, but merely to clarify and exemplify the invention. For a more complete understanding of the present invention, reference is now made to the following drawings in which:

FIG. 1 is a schematic depiction of the centrifugal flow gas within the ion spray chamber according to this invention.

FIG. 2 is a full sectional view of the electrospray assembly, as well as the LC column, union and MS inlet capillary according to the preferred embodiment of the present invention.

DESCRIPTION OF THE PREFERRED EMBODIMENT

As required, detailed illustrative embodiments of the present invention are disclosed herein. However, techniques, systems and operating structures in accordance with the present invention may be embodied in a wide variety of sizes, shapes, forms and modes, some of which may be quite different from those in the disclosed embodiments. The specific structural and functional details disclosed herein are merely representative, yet in that regard, they are deemed to afford the best embodiment for purposes of disclosure and to provide a basis for the claims which define the scope of the present invention.

The following presents a detailed description of a preferred embodiment of the present invention, as well as some alternate embodiments of the invention. As discussed above, the present invention relates generally to the mass spectroscopic analysis of chemical samples and more particularly to the coupling of liquid chromatography (LC) equipment to mass spectrometry (MS) equipment. Specifically, an apparatus and method are described for the production of ions and subsequent transport of said ions into a MS. Reference is herein made to the figures, wherein the numerals representing particular parts are consistently used throughout the figures and accompanying discussion.

Figure 3:
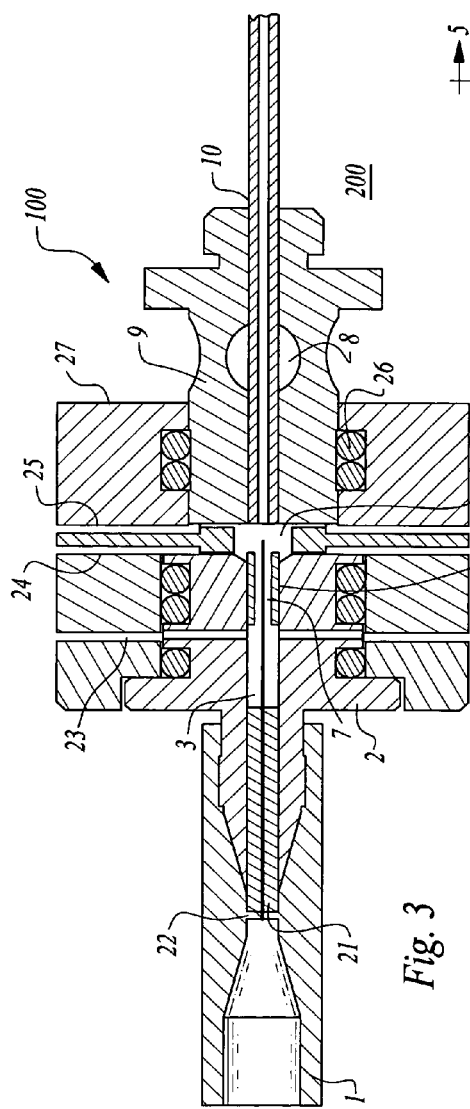
FIG. 3 is a more detailed full sectional view of the electrospray insert within the assembly that is coupled with the union and MS inlet capillary according to the preferred embodiment of the present invention.

As shown in FIGS. 1, 2 and 3, the ion injection spray device 100 resides between an LC column or other connection tubing 11 from a fluid flow source 15 (FIG. 1) and a MS 200 capillary inlet 10. The ion spray 100 is housed in a non-conductive body 14, which supplies gas and voltage inputs and holds the entire assembly in place. Liquid phase samples introduced at the liquid flow source 15 have been separated (such as in an LC column) and exit the flow source 15 into the conductive union 1 through the connection tubing 11. Within the union 1, a high voltage liquid junction 21 is formed in the "Zero Dead Volume" (ZDV) center 22 of the conductive union 1. High voltage is supplied through a connector 12 and a conductive electrode 4 to the conductive union 1.

The charged liquid exits the conductive union 1 through an ion spray needle 3 which is attached to the conductive union 1. The needle 3 is supported by a non-conductive tip housing 2 (FIG. 2) and exits the needle 3 outlet in the ion injection spray chamber 6 where electrospray of the charged liquid takes place. The chamber 6 is formed between the non-conductive needle housing 2 and the MS capillary inlet 10, which are surrounded by the gas distribution manifold 27.

The MS capillary inlet 10 is preferably fitted with a mounting flange 9 to seal it to the gas distribution manifold 27 using O-rings 26 and the non-conductive needle housing 2 is also sealed in the gas distribution manifold 27 using O-rings. The vent holes 8 on the mounting flange 9 provide tip cooling and temperature differential when using a heated MS capillary inlet 10. This design lowers the temperature in the ion injection spray chamber 6 and reduces the chance of sample precipitation that could cause the spray tip to clog when using a heated capillary MS inlet 10 at elevated temperatures.

The gas distribution manifold 27 (FIGS. 3 and 4) is designed to distribute gas from the gas input 13 (FIGS. 1 and 2) to the chamber 6 using the vacuum of the MS 200. The first vacuum assisted coaxial gas flow 33 (FIG. 4) is introduced through a rear opening 23 in the gas distribution manifold 27 around the needle 3. The gas flow 33 enters an annular space 7 (FIGS. 3 and 4) between the needle 3 and a non-conductive outer tube 5 at high velocity, as developed by the vacuum inlet of the MS. The outer tube 5 and the coaxial gas flow annular space 7 are specifically designed to assist electrospray and prevent large droplets from forming at the tip of the needle 3.

In the preferred embodiment, the needle 3 is made of fused silica capillary tubing. The non-conductive needle housing 2 and non-conductive outer tube 5 are made of PEEK. The union 1 is made of metal. Due to the high voltage involved, the silica tubing is sufficiently electrically conductive to facilitate ion formulation.

A second vacuum assisted gas flow 34 (FIG. 4) is preferably introduced through a middle opening 24 in the gas distribution manifold 27 (FIG. 3) at the needle 3 tip to focus the spray from the tip inward. This second gas flow 34 can be introduced radially toward a central axis X (FIGS. 4 and 5) of the chamber 6 or introduced in a centrifugal fashion at least partially circumferentially about the central axis X.

A third vacuum assisted gas flow 35 (FIGS. 4 and 5) is preferably introduced through a front opening 25 in the gas distribution manifold 27. The third gas flow 35 is introduced in a centrifugal fashion to provide funnel shaped swirling gas flow 37 to help desolvate and focus the sample ions 36 into the MS 200, 210.

The gas flow 35 and any other gas flows into the ion spray chamber 6 can be introduced in a centrifugal fashion in a variety of different ways. In one form of the invention, the gas flow 35 comes in through a front opening 25 which is broken into separate outlets (FIG. 5) at the junction between the chamber 6 and the front opening 25, which gas entry ports are offset laterally from a center line X of the chamber 6. If more than one entry port for the gas flow 35 is provided, they are preferably offset in a common direction, such as each being offset to a left side of the center line X of the chamber 6 when viewed in a common direction with the direction of flow of ions through the chamber 6.

Figure 5:
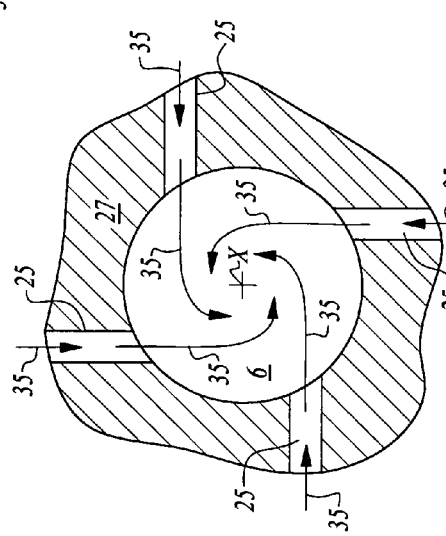
FIG. 5 is a sectional view taken along line 5-5 of FIG. 4 or FIG. 6 and showing the off center inlet embodiment to induce centrifugal gas flow within the chamber.

In such an instance, the gas flow 35 into the chamber 6 would be centrifugal and curving in a counter-clockwise direction (along arrows 35 of FIG. 5). The flow would transition from being centrifugal within a plane perpendicular to the centerline of the chamber 6 into axial in a common direction with flow of ions through the chamber 6 as the centrifugal gas flow 35 is drawn into the vacuum within the MS 200, 210 (FIGS. 1-3). Thus, the flow would actually be in somewhat of a funnel transitioning from purely centrifugal to primarily axial. This funnel-like flow helps to keep all of the ions exiting the tip of the needle 3 in a tight column adjacent the central axis X of the chamber 6, and passing from the tip of the needle 3 into the capillary inlet 10 of the MS 200, 210.

As another alternative, centrifugal flow into the chamber 6 can be achieved by forming vanes in walls of the forward opening 25 or other openings in which it is desired that the gas flow be at least somewhat centrifugal. Such veins could be fixed and curve in the direction desired for swirl within the chamber 6. As another alternative, the veins could be formed on a rotor which would spin to generate the centrifugal flow as desired. While more complex, such a rotor could be varied in speed to allow for adjustment in the degree of centrifugal flow within the chamber 6.

Most preferably, at least one gas flow, typically the most upstream gas flow 33 is configured to be primarily coaxial with the centerline of the chamber 6 and the centerline of the needle 3. At least one downstream gas flow (and two gas flows 34, 35 in the embodiment of FIGS. 1-3) is provided in a more centrifugal fashion than the first primarily coaxial gas flow. However, in simplified or varied forms of this invention the gas flow might be limited to as few as one gas flow with at least some centrifugal component (FIG. 1) to the gas flow about the centerline of the chamber 6 and the needle 3, and still provide some benefit according to this invention.

Figure 4:
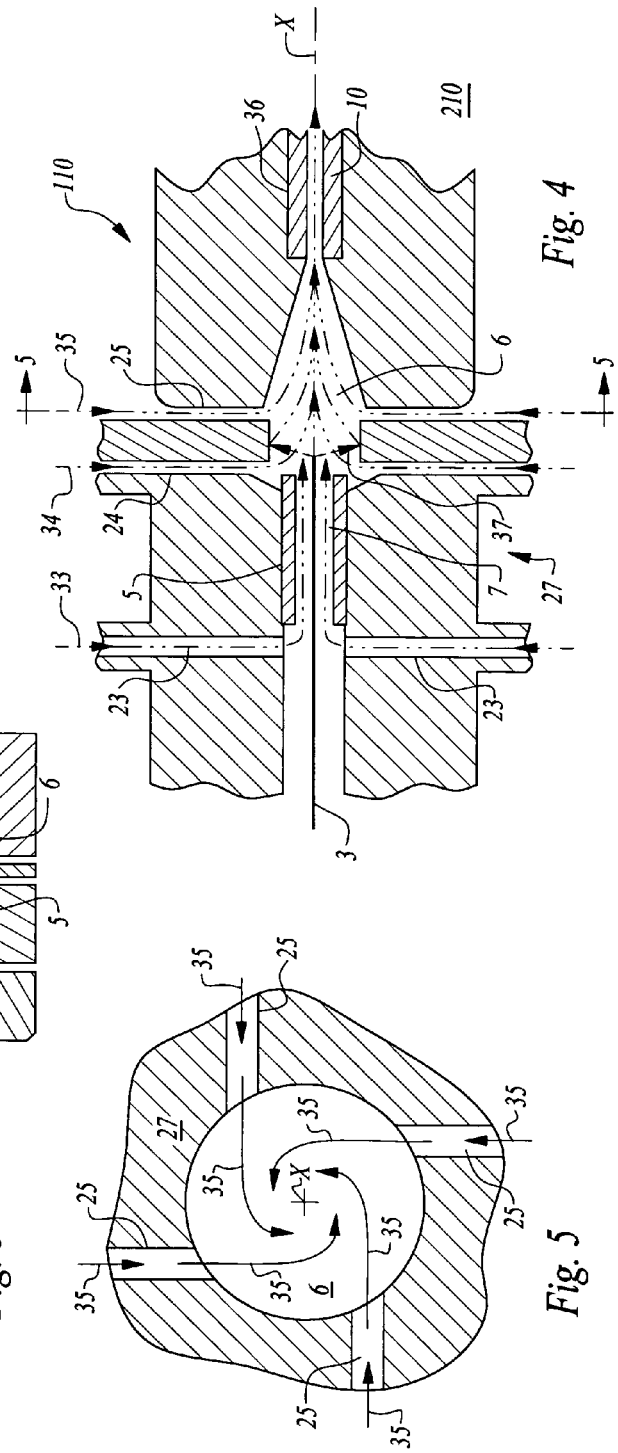
FIG. 4 is a full sectional most detailed view of gas flow paths of the electrospray insert around the spray needle into the mass spectrometer at the electrospray chamber and for a slightly modified embodiment of the invention.

While FIG. 4 depicts a more detailed view of the chamber 6 generally similar to the ion injection spray device 100 of FIGS. 2 and 3, FIG. 4 actually depicts a slightly modified embodiment in that the inlet end of the MS 210 has a tapering conical form about a central axis X of the capillary inlet 10 of the MS 210 and a diameter of the chamber 6 has been altered slightly. The diameter of the chamber 6 can be customized to coordinate with the configuration of the inlet end of the particular MS with which the ion injection spray device 100, 110 of this invention is configured to operate with. Also, conceivably for different specific ions it might be desirable to provide custom different sizes for the chamber 6 which would further optimize injection of the ions into the MS in a tight column adjacent the central axis X of the chamber 6 and with a minimum of sample loss.

Figure 6:
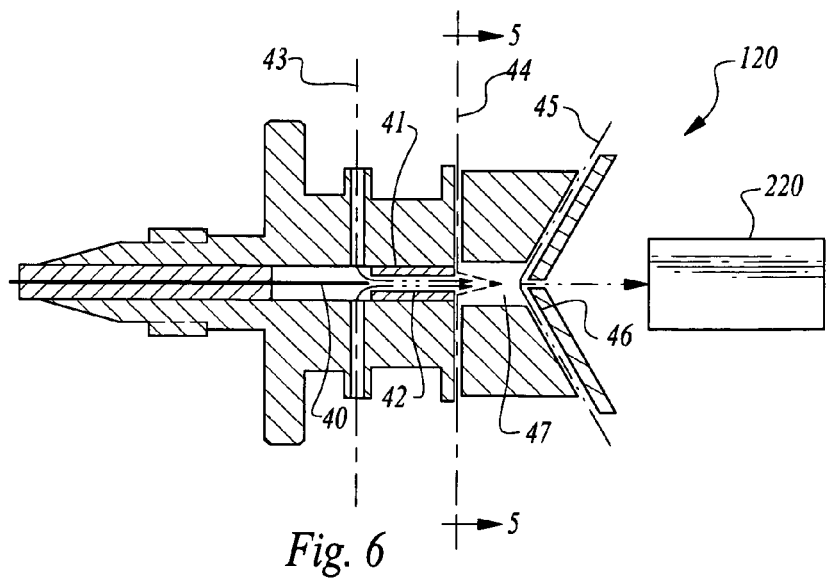
FIG. 6 is a full sectional view depicting an alternative design of the present invention for use with mass spectrometers that use an orifice as the ion inlet.

While the voltage for the ion injection spray device 100, 110 can be provided in a variety of different ways, often the most convenient manner for providing such voltage is to utilize high voltage leads from the MS 200, 210, 220 (as depicted in FIG. 6). In this way, the proper desired potential difference is provided between the relevant portions of the MS 200, 210, 220 and the union 1 where the sample is initially caused to experience a voltage which ultimately leads to ionization of the sample as it leaves the tip of the needle 3. Depending on the particular voltage provided by the MS 200, 210, 220, and other design parameters for the ion injection spray device 100, 110, 120, 53, the material forming the needle 3 can also be adjusted to optimize formation of ions from the sample. For instance, the needle could be formed of fused silica as is common with nanospray mass spectrometry. As an alternative, the spray needle could be made of metal capillary tubing or polymeric capillary tubing, altering the electric performance of the needle 3 and tuning the ion injection spray device 100, 110, 120, 53 to the particular configuration of the MS 200, 210, 220 and other design parameters of the device 100, 110, 120, 53. Depending on the material and other design parameters of the needle 3, the voltage can optionally be adjusted as a further design parameter for optimization of the device 100, 110, 120, 53.

Other details of the needle 3 could also be modified as design parameters to optimize for different performance characteristics desired for the ion injection spray device 100, 110, 120, 53. For instance, while the needle 3 preferably has both a cylindrical inner diameter and outer diameter along its length, the needle 3 could have tapering inner and/or outer diameters. Also, a difference between the inner and outer diameters can vary so that a thickness of the wall of the needle 3 can be selected to optimize performance. For instance, decreasing the wall thickness of the needle 3 at the tip can cause greater charge concentration at the tip, effecting ionization of the sample as it leaves the needle 3. Modifying the inside diameter of the needle 3 affects flow rate of the sample and thus affects throughput through the MS 200, 210, 220 and duty cycle for the LC/MS system.

The needle 3 is preferably supported adjacent the union 1 so that the needle 3 does not contact the needle housing 2 or the outer tube 5. This support for the needle 3 is upstream of where the rear opening 23 in the gas distribution manifold 27 allows the first coaxial gas flow 33 to approach the needle 3 and pass coaxially along an exterior of the needle 3 and toward the chamber 6. This mount for the needle 3 is preferably fixed. As an alternative, this mount for the needle 3 can be adjustable so that a position of the tip of the needle 3 can be adjusted axially along the center line X to bring it closer to the capillary inlet 10 of the MS or further from the capillary inlet 10 of the MS. Such needle position adjustability provides a further parameter which can either be designed into the ion injection spray device 100, 110, 120, 53 or configured to be adjustable for tuning of the device 100, 110, 120, 53.

The typically un-tapered inner diameter of the spray needle 3 is typically 0.02-0.05 millimeters, and its typically un-tapered outer diameter is typically 0.05-0.15 millimeters. The inner diameter of the outer tube 5 is typically 0.15 to 0.25 millimeters, leaving an annular space between the two tubes of thickness about 0.05 to 0.10 mm. The outer diameter of the outer tube is not critical and the outer tube can be made of any desired thickness depending on the material from which it is formed. Typically the outer tube is made of PEEK and the tip of the spray needle typically protrudes 1-5 mm from the outer tube.

FIG. 6 shows an alternative embodiment of the ion injection spray device 120 for use with MSs that utilize a MS inlet orifice 46 rather than a MS capillary inlet 10. This embodiment consists of a non-conductive ion injection spray needle 40, a non-conductive outer cylinder 41, focusing coaxial gas flow 42, entering upstream of the needle 40 tip and centrifugal gas flow 44 generally near the tip to help desolvate and focus the desolvated sample ions 47 into the MS. A curtain gas 45 from the MS 220 may also be used to help desolvate and focus sample ions.

Figure 7:
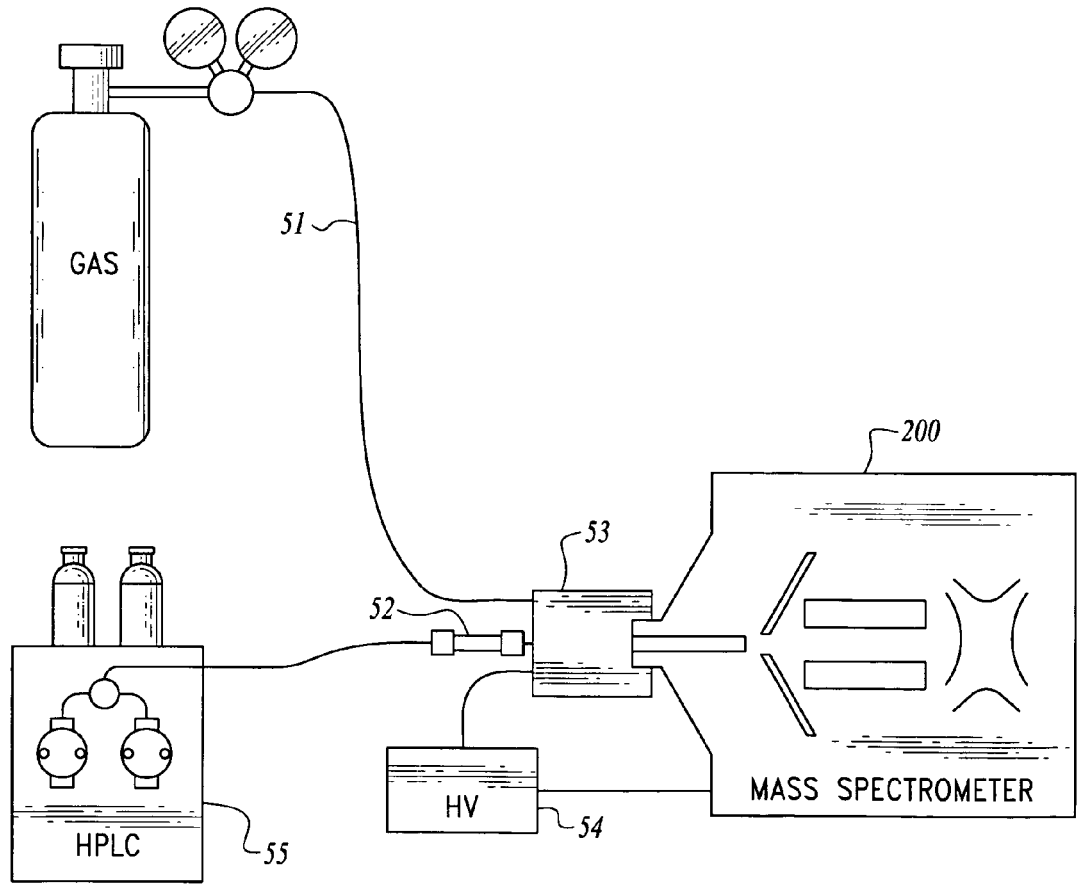
FIG. 7 is a schematic of a typical LC/MS injections system of this invention incorporated therein.

FIG. 7 depicts a typical LC/MS system for use with the present invention. A HPLC or other liquid separation device 55 provides liquid phase sample flow through a separation column 52 to the ion injection spray device 53 and into the MS 200. An optional gas source 51 can be used to supply gas to the device 53. Although ambient air can also be used as the gas source pulled in by the MS 200 vacuum, high purity gas (nitrogen, air, helium, etc.) is recommended when contaminants are present in the ambient air around the MS 200. Ambient air or high purity gas may also be presaturated with solvent vapors (methanol, formic acid, ammonia, etc.) for specific types of MS 200 analytes which respond better in the presence of such solvent vapors. A high voltage supply 54 from the MS 200 provides the necessary voltage differential for electrospray ionization of the liquid sample.

It should be noted that any other method known in the prior art might be used in conjunction with the device according to the present invention. For example, the ion inlet could be an orifice, a glass capillary or a metal capillary and the high voltage could be applied on the MS inlet while the spray tip is at ground potential.

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. When structures are identified as a means to perform a function, the identification is intended to include all structures which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. A liquid chromatography and mass spectrometry sample analysis system comprising in combination:
    at least one liquid chromatography column adapted to elute a sample into separate constituents;
    a high voltage interface to convert sample constituents into ions;
    a mass spectrometer having an inlet for ions from said high voltage interface;
    said mass spectrometer adapted to maintain sub-atmospheric pressure therein and adapted to evaluate the mass-charge characteristics of ions in the sample;
    said high voltage interface including a spray needle with a base and a tip, said base in fluid communication with an outlet of said liquid chromatography column for acceptance of a liquid flow, said tip closer to said mass spectrometer inlet than said base;
    said needle tip located within a chamber upstream of said mass spectrometer inlet and substantially aligned along a common central axis with said mass spectrometer inlet;
    said chamber being adapted to be substantially sealed to the mass spectrometer inlet and having a pressure greater than said pressure within said mass spectrometer, such that flow is induced from said chamber into said inlet of said mass spectrometer; and
    at least one gas flow inlet into said chamber, said at least one gas flow inlet adapted to introduce gas into said chamber at least partially circumferentially relative to said central axis of said needle tip and said mass spectrometer inlet to help desolvate and focus the ions into the mass spectrometer inlet.

2. The system of claim 1 wherein said high voltage interface includes a voltage between said tip of said needle and said inlet of said mass spectrometer.

3. The system of claim 2 wherein said needle is electrically coupled to a conductive union supporting said base of said needle, said conductive union having a voltage potential difference relative to said mass spectrometer inlet.

4. The system of claim 1 wherein a plurality of gas flow inlets are provided into said chamber, a first of said gas flow inlets located upstream of said needle tip and oriented to cause substantially co-axial flow of the gas adjacent said needle tip in a direction common with flow of sample constituents out of said needle tip, and a second gas flow inlet downstream of said first gas flow inlet, said second gas flow inlet adapted to introduce gas into said chamber at least partially circumferentially.

5. The system of claim 4 wherein said second gas flow inlet is located downstream of said needle tip.

6. The system of claim 5 wherein a third gas flow inlet into said chamber is provided between said first gas flow inlet and said second gas flow inlet, said third gas flow inlet located adjacent said tip and oriented substantially radially inward toward said central axis.

7. The system of claim 4 wherein a third gas flow inlet is provided adjacent said mass spectrometer inlet, said third gas flow inlet configured as a curtain inlet for said mass spectrometer.

8. The system of claim 1 wherein said at least one gas flow inlet into said chamber includes vanes which act on the flow of gas passing the vanes to cause the gas to enter the chamber swirling at least partially circumferentially about said central axis.

9. The system of claim 1 wherein said at least one gas flow inlet into said chamber is spaced laterally relative to said central axis so that gas entering said chamber through said gas flow inlet swirls circumferentially somewhat about said central axis.

10. The system of claim 1 wherein said needle is formed at least partially of fused silica.

11. The system of claim 2 wherein said needle is formed at least partially of metal.

12. The system of claim 1 wherein said needle is formed at least partially of PEEK.

13. The system of claim 1 wherein said needle is adapted to be adjustably positioned axially along said central axis such that said tip of said needle can be positioned at different distances away from said inlet of said mass spectrometer.

14. The system of claim 1 wherein said gas flow inlet is coupled to a source of gas that includes air.

15. The system of claim 1 wherein said gas flow inlet is coupled to a source of gas taken from the group of gas sources including nitrogen and helium.

16. The system of claim 1 wherein said gas flow inlet is coupled to a source of gas including a saturated solvent within said gas.

17. An ion injection spray system for delivering sample ions into an inlet of a mass spectrometer, the ion injection spray system comprising in combination:
    an injection spray needle having a base end adapted to be coupled to a sample source for acceptance of a liquid flow and a tip opposite said base, said tip adapted to be located closer to the mass spectrometry inlet than said base;
    a chamber surrounding said tip of said needle, said chamber is adapted to be substantially sealed to the mass spectrometry inlet with the mass spectrometer having an at least partial vacuum therein, such that flow is induced from said chamber into the mass spectrometry inlet;
    a voltage between said needle and a reference, said voltage sufficient to ionize sample constituents exiting said tip of said needle;
    a first gas flow inlet into said chamber, said first gas flow inlet oriented to introduce gas substantially coaxially to the centerline of said needle; and
    a second gas flow inlet into said chamber, said second gas flow inlet oriented to introduce gas substantially radially to the centerline of said needle to focus the spray inward.

18. The ion injection spray system of claim 17 wherein at least three gas inlets are provided into said chamber including said first gas flow inlet, said second gas flow inlet and a third gas flow inlet, said second gas flow inlet oriented between said first gas flow inlet and said second gas flow inlet, said third gas flow inlet oriented to introduce gas at least partially circumferentially relative to the centerline of said needle.

19. The ion injection spray system of claim 17 wherein said first gas flow inlet is located upstream of said tip of said needle with said first gas flow inlet attaining a substantially completely co-axial orientation relative to said needle tip as said first gas flow inlet approaches said needle tip.

20. The ion injection spray system of claim 17 wherein said voltage is established between said needle and said reference, with said reference being a portion of a mass spectrometer downstream of said chamber.

21. A method for ion spray injection, including the steps of:
    providing an ion injection spray needle having a base end adapted to be coupled to a sample source for acceptance of a liquid flow and a tip end opposite the base, the tip end closer to a mass spectrometer inlet than the base;
    locating the needle tip within a chamber, the chamber surrounding the tip of the needle;
    sealing the chamber to the mass spectrometer inlet downstream of the chamber with pressure in the chamber higher than pressure in the mass spectrometer, such that flow is induced from said chamber into the mass spectrometry inlet;
    applying a voltage between the needle and a reference, the voltage sufficient to ionize sample constituents exiting the tip of the needle;
    inputting a coaxial gas flow upstream of the needle tip and past the needle tip to induce coaxial flow adjacent the tip; and
    inputting a radial gas flow into the chamber adjacent the needle tip to focus the spray inward.

22. The method of claim 21 including the further step of additionally inputting a centrifugally swirling gas into the chamber.

23. The method of claim 22 including the further step of establishing the gases entering the chamber from a common gas source.

24. The method of claim 21 including the further step of coupling the needle base to an output of a liquid chromatography device and coupling the chamber to a mass spectrometry inlet, such that the ion spray injection links the liquid chromatography device to the mass spectrometer.

25. The injection system of claim 17 wherein at least one gas flow inlet is coupled to a source of gas comprising presaturated solvent vapor.

26. The injection system of claim 25 wherein the solvent is one of: methanol, formic acid and ammonia.

27. The injection system of claim 17 wherein the injection spray resides between a liquid chromatography column or a connection tubing from a fluid flow source and the inlet of the mass spectrometer.

28. The injection system of claim 17 wherein the chamber at the mass spectrometry inlet has a tapering conical form.

29. The method of claim 21 wherein at least one gas flow comprises a presaturated solvent vapor.

30. The method of claim 29 wherein the solvent is one of methanol, formic acid and ammonia.

* * * * *